(12) United States Patent
Arnold et al.

(10) Patent No.: US 6,248,323 B1
(45) Date of Patent: *Jun. 19, 2001

(54) DIETARY SUPPLEMENTATION WITH AND METHODS FOR PREPARATION OF YEAST-DERIVED CHROMIUM SALTS

(75) Inventors: Michael Arnold, Irvine; Ping Yang, Fullerton, both of CA (US)

(73) Assignee: VIVA Life Science, Inc., Costa Mesa, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/760,897

(22) Filed: Dec. 6, 1996

Related U.S. Application Data

(63) Continuation-in-part of application No. 08/719,572, filed on Sep. 25, 1996, now Pat. No. 6,140,107.

(51) Int. Cl.[7] ............... A01N 63/04; C12N 1/16; C12N 1/18; A23L 1/28
(52) U.S. Cl. .................. 424/93.51; 435/255.1; 435/255.2; 435/255.21; 435/940; 435/942; 426/62
(58) Field of Search ........... 424/93.51; 426/62; 435/255.1, 255.2, 255.21, 940, 942

(56) References Cited

U.S. PATENT DOCUMENTS

| | | | | |
|---|---|---|---|---|
| 4,343,905 | * | 8/1982 | Szalay | 435/255.21 |
| 4,348,483 | * | 9/1982 | Skogerson | 426/74 |
| 4,923,855 | * | 5/1990 | Jensen | 514/188 |

FOREIGN PATENT DOCUMENTS 61-158776 * 7/1986 (JP) .

OTHER PUBLICATIONS

Vinson et al. Nutri. Reports Intern. vol. 30(4), pp. 911–918. 1984.*

* cited by examiner

*Primary Examiner*—Christopher R. Tate
(74) *Attorney, Agent, or Firm*—Lyon & Lyon LLP

(57) ABSTRACT

The present invention solves the need for non-toxic forms of bioactive chromium which is an essential part of the human diet. This invention provides novel dried-yeast products containing chromium as well as a method of producing the dried yeast products. The method uses organochromium complexes comprised of trivalent chromium, nicotinate, and glycine having high Glucose Tolerance Factor chromium activity. The invention also provides nutritional supplements containing the novel chromium-containing dried-yeast products and methods of administering these products and supplements to increase glucose uptake and insulin binding.

19 Claims, No Drawings

DIETARY SUPPLEMENTATION WITH AND METHODS FOR PREPARATION OF YEAST-DERIVED CHROMIUM SALTS

CROSS-REFERENCE TO RELATED APPLICATION

This is a continuation-in-part of application Ser. No. 08/719,572, now U.S. Pat. No. 6,140,107, filed Sep. 25, 1996.

BACKGROUND OF THE INVENTION

1. Field of the Invention

This invention relates to the field of human dietary supplements, and more specifically to improved supplements comprising organochromium complexes derived from yeast.

2. Background

The physiological assimilation of an adequate quantity of heavy metals is essential to human health. Failure to ingest and absorb the necessary amounts of such metals can lead to improper functioning of the body's metabolic processes, and to various diseases and disorders. In particular, chromium deficiency can be a major problem in the human diet. Inadequate intake of chromium has been linked to an increased risk of heart disease, diabetes, hypoglycemia, obesity, impaired metabolism, and diminished longevity. Heart disease and diabetes alone account for about sixty percent of all deaths in the United States each year, and death usually strikes these victims ten to twenty years before they reach the average life span. The National Academy of Sciences has recommended an intake for humans of about 50 to 200 micrograms of trivalent chromium daily. It has been reported that about 9 out of 10 adults fail to ingest even the minimum recommended amount.

Trivalent chromium ($Cr^{3+}$) describes the charged state of chromium species present in foods and, thus, supplementation with $Cr^{3+}$ is useful in dietary supplements. Other forms of chromium, such as $Cr^{4+}$ and $Cr^{6+}$, are quite toxic and are not useful in supplementing the human diet. Trivalent chromium may be complexed to organic or inorganic ligands, forming organic and inorganic forms of trivalent chromium respectively. Both organic and inorganic forms of chromium have been used as dietary supplements.

Biological activity of chromium is highly dependent upon the type of coordinate complex formed with the chromium. A chromium coordinate complex is formed when an organic ligand is bound to trivalent chromium in a configuration that involves both covalent/ionic and non-covalent forces to stabilize the complex. The biological activity of a complex depends upon its bioavailability. Inorganic chromium compounds have been shown to have much less bioavailability than organic coordination compounds. [M. M. Wang et al., Nutr. Res., 9:989–998 (1989)]. A possible explanation is that since organic chromium complexes have greater membrane solubility than their inorganic counterparts, organic complexes have better bioavailability and, hence, have higher biological activity.

One of the major nutritional roles of trivalent chromium appears to be its effect in glucose metabolism. Specifically, a deficiency in chromium in the diet has been linked to impaired glucose tolerance, i.e., reduced ability to maintain blood glucose at normal levels. The transport of glucose and vital amino acids into the cell for energy and protein synthesis is facilitated by the binding of insulin, which is an important hormone for the human system since it is involved in the control of muscle growth, body weight, cardiovascular health and many other vital metabolic functions. Mertz has shown that an organic trivalent chromium complex called Glucose Tolerance Factor ("GTF") is responsible for binding insulin to cell membrane insulin receptor sites. [Mertz, W., "Chromium Occurrence and Function in Biological Systems," Physiol. Rev., 49:163–239 (1969), "Mertz I"]. The exact structure of active yeast-produced GTF is not well defined. However, chemical analysis of GTF shows that GTF is comprised chiefly of trivalent chromium and niacin, and contains glycine, glutamic acid, and cysteine. [Evans, G. W., et al., Biochem. Biophys. Res. Comm., 50:718–722 (1973)]. Hence, chromium having GTF chromium activity is essential to the maintenance of blood glucose levels.

3. Description of Prior Art

Since the human diet is frequently deficient in chromium content, dietary supplementation with highly bioavailable, non-toxic chromium agents is desirable. A major shortcoming of using Brewer's yeast as a source of naturally occurring GTF as supplemental dietary chromium is that the active form of chromium ion is formed in very low concentrations in Brewer's yeast. As a result, the average human would have to consume at least ten tablespoons of Brewer's yeast per day in order to get about 40 micrograms of biologically active chromium. Attempts at extracting or concentrating GTF from Brewer's yeast have been reported as reasonably successful, but the expense of the processing required for producing a commercial food supplement by these methods is prohibitive for the development of a viable commercial product. [Toepfer, E. et al., J. Agr. Food Chem., 21(1): 69–73 (1973) "Toepfer I"]. Thus, inorganic and organic complexes of trivalent chromium have been developed with hopes of providing safe alternative sources of supplemental chromium having similar biological activity to GTF derived from Brewer's yeast.

The prior art provides for dietary chromium which can be used to supplement the diet from two distinct sources: chemical synthesis (of inorganic and organic forms of chromium) or biological processing by yeast (chromium-enriched yeast). Although synthetic inorganic chromium compounds, such as chromium chloride, chromium oxide, and chromium acetate, have been shown to have very low bioavailability, they do show limited activity as dietary supplements. [Anderson, R. and Kozlovsky, A., Am. J. Clin. Nut., 41:1177–1183 (1985); Liu, V. J. K., et al., Am. J. Clinical Nutrition, 31:972–976 (1978)]. Unfortunately, these inorganic chromium compounds have also been shown to have appreciable toxicity to the human system. [Mertz, W., Newer Trace Elements in Nutrition, 7:123–159 (1971) "Mertz II"].

Trivalent chromium complexed with various organic ligands has been used to adequately supply chromium to the human body. Experiments have shown that some of these chromium complexes are better absorbed and utilized by the body than elemental or inorganic salt forms of chromium. [See, e.g., Evans, U.S. Pat. No. 4,315,927]. However, a major shortcoming of the compounds in which trivalent chromium is complexed with organic ligands, specifically, picolinic acid, is their inherent water insolubility. Such insolubility may hinder the efficacy or absorption of chromium by intestinal membranes, ultimately leading to only a fraction of the chromium being available to effect its nutritionally beneficial actions. Another drawback of using chromium picolinates as dietary supplements is the potential for chromosomal damage when the complexes are introduced into cells. [Brody, J., "Chromosome Damage in the Lab is Tied to a Chromium Supplement," New York Times, Oct.

25, 1995]. Nicotinate salts of trivalent chromium have also been used for supplementation to the human diet. These chromium nicotinate compounds have demonstrated biological action in some experiments, however, they show decreased activity in some key metabolic assays where the efficiency of chromium metal uptake by the human intestine was investigated. [See, Evans, cited above].

Attempts to obtain compounds with appreciable GTF biological activity have also been made. [Toepfer, et al., *J. Ag. Food Chem.*, 25(1):162–166 (1977) "Toepfer II"]. Toepfer teaches the reaction of nicotinic acid and amino acids with chromium chloride in refluxing alcohol. However, the biological activity of these compounds are marginal, the reflux reaction generates limited yields, and the products are hard to characterize and are of limited stability. A method for synthesizing a trivalent organochromium species comprised of contacting an alkali metal salt of nicotinic acid with a trivalent chromium salt is known. [Jensen, U.S. Pat. No. 4,923,855]. The resulting chromium complex is a form of chromium that is purportedly a useful supplement to the human diet since it has been demonstrated to have GTF activity comparable to Brewer's yeast. However, this complex has poor solubility.

Chromium complexed with various amino acids has also been reported. Certain chelated compounds can be used as feed supplements for animals. [See, e.g., Ashmead, U.S. Pat. No. 4,020,158]. Specific buffer systems have been used to derive ligands for trivalent chromium from hydrolyzed protein concentrates in the production of feed supplements for animals. [See, Jenson, U.S. Pat. No. 4,187,364]. Trivalent chromium complexed with a vitamin ligand, e.g., nicotinic acid and, optionally, an α-amino acid have been prepared. [Ashmead, U.S. Pat. No. 5,292,729]. Such compounds have appreciable biological activity similar to Brewer's yeast.

Most notably, Brewer's (or Baker's) yeast also contains active forms of trivalent chromium. The terms Brewer's and Baker's yeast are known in the art to refer to the same strain of yeast. It has been shown that Glucose Tolerance Factor (GTF) from Brewer's yeast is an effective form of chromium that is essential for human metabolism. [See, Mertz *Archives of Biochem. and Biophvs.*, 85:292–295 (1959), "Mertz III"]. GTF can be produced by niacin or tryptophan, glycine, glutamic acid and cysteine, as well as a source of chromium, usually inorganic chromium. The trivalent chromium complexes naturally produced in low yields in Brewer's yeast are known to be highly active. Indeed, the most active source of naturally occurring chromium is found in Brewer's yeast. [Mertz, W., *Present Knowledge in Nutrition*, 36:365–372 (1976), "Mertz IV"].

Other forms of chromium yeast have been reported. For example, chromium derived from Brewer's yeast has reported chromium concentrations of about ten to thousand-fold greater than those of Mertz IV (cited above) has been produced. [See, Skorgerson, U.S. Pat. No. 4,348,483]. A method of concentrating organic chromium complex in Brewer's yeast comprising a nutritional media of chromium oxide, and specific quantities of certain amino acids has been reported. [See, Szalay, U.S. Pat. No. 4,343,905]. These sources of biologically active chromium are obtained by the processing of yeast having an enriched chromium content. It is believed that these processed "chromium yeast" have a much greater concentration of chromium than is naturally occurring in Brewer's yeast, which is typically about 5 ppm. [Offenbacher, E., *Am. J. Clinical Nut.*, 42:454–461 (1985)]. As reported, these chromium-yeast metabolically process the chromium, thereby producing chromium coordination complexes with high GTF activity.

Inorganic forms of chromium have been used as feed for yeast in order to produce these chromium coordination complexes of high GTF activity. For example, a method for producing chromium-enriched yeast (Brewer's yeast, Torula yeast, or *S. uvarum*) that employs an aqueous solution of inorganic chromium salts such as $CrCl_3$ with growth media, and with a pregrowth incubation period to cultivate the yeast is known. [Skogerson, U.S. Pat. No. 4,348,483]. Chromium content of the yeast produced using this process is from about 500 ppm to about 1,000 ppm. However, this process entails internalization of the inorganic chromium salt without complete metabolization, resulting in a high probability that a significant amount, if not all, of the chromium found in the chromium-enriched yeast is inorganic chromium. Hence, the chromium produced in this process is not GTF active chromium yeast, but is rather inorganic trivalent chromium salts mixed with the structural material of yeast. As such, the chromium produced using this method does not possess high bioactivity and is also toxic if ingested in high doses.

A method is also known for producing Brewer's yeast having an intracellular chromium concentration of about 200 ppm by cultivating the yeast in a broth where the source of trivalent chromium is from a mixture of chromium oxide and certain amino acids. [Szalay, U.S. Pat. No. 4,343,905]. Although 80% of the chromium produced by this method is reported to be GTF chromium, this method is hard to reproduce due to the insolubility of the chromium oxide. In other words, the insolubility of chromium oxide results in a low yield of GTF chromium produced by this method. To the extent that this method also involves internalization of chromium oxide without its metabolization, it results in inorganic chromium oxide that is merely mixed with the yeast structural material. Since chromium oxide is known to be significantly toxic to the human system, this method is not preferred as a method for making a dietary supplement.

There remains a need in the art for concentrated forms of GTF chromium—complexes bearing the structure and activity found in naturally occurring Brewer's yeast, but having a higher biological activity, and which may be used in high concentrations because of their low toxicity. In addition, there is a need in the art for methods to produce such complexes.

SUMMARY OF THE INVENTION

The present invention overcomes the shortcomings of the prior art by providing a method for producing a composition of highly active GTF chromium, where: (1) the chromium source of the present invention is the natural form of active GTF chromium coordination complex; (2) the chromium source is substantially organometallic chromium, completely free of inorganic chromium; (3) the coordination complex of trivalent chromium is substantially metabolizable by the human system; and (4) the process can be carried out efficiently and in a manner that meets requirements important for commercial production.

We have now discovered a preferred nutritional source of trivalent chromium for improved delivery of the physiologically important trace metal coordination complex, GTF chromium. This discovery is based on the method of growing Brewer's yeast (*S. cerevisiae*) in the presence of the chromium complex having at least one mole of trivalent chromium coordinated with at least one mole of nicotinate and at least one mole of an amino acid (e.g., glycine). An example of such a complex is Chromium Chelavite® and is commercially available from Albion Laboratories, Inc. The resulting yeast is enriched with appreciable amounts (between 1,000 ppm and 6,000 ppm) of chromium. The dried chromium yeast mass shows high levels of GTF activity, much greater than in naturally occurring Brewer's yeast.

Hence, a first object of the present invention is to provide a method of preparing in yeast organochromium complexes with high GTF activity.

Another object of the present invention is to provide an improved synthetic form of yeast-derived GTF chromium that is substantially similar to the GTF chromium complexes found naturally occurring in the Brewer's yeast extract. A further object of the present invention is to provide an improved synthetic form of yeast-derived GTF chromium that is characterized by its high biological activity for the stimulation of glucose uptake and the binding of insulin. Hence, it is another object of the invention to increase glucose uptake and insulin binding in humans using the novel yeast-derived chromium compounds of the invention.

It is a further object of the present invention to provide a method for the production of chromium-enriched yeast, where the source of chromium for metabolism by the yeast is a trivalent chromium chelate complex of niacin and glycine.

It is a further object of the present invention to provide a form of yeast-derived trivalent chromium species that is essentially non-toxic to the human body.

It is another object of the present invention to provide a method of administering the yeast-derived trivalent chromium compositions of the present invention to the human body to promote good nutritional health.

It is a further object of the present invention to provide a method of increasing fat metabolism in the human body by administration of the yeast-derived chromium complexes of the present invention.

Another object of the present invention is to provide a method of reducing susceptibility of the human body to chronic disorders such as heart disease and diabetes via administration of the yeast-derived trivalent chromium complexes of the present invention.

DETAILED DESCRIPTION OF THE INVENTION

The present invention relates to novel methods of cultivating yeast in a solution containing an organochromium complex as the source of external chromium. The organochromium complex solution comprises one mole of chromium salt with two moles of nicotinate and one mole of glycinate. Cultivation in yeast followed by purification and isolation of a dried yeast product yields a dried yeast mass having an enriched content of trivalent chromium possessing high biological activity. This dried yeast mass may then be used as a nutritional supplement for the human diet.

Hence, the present invention provides a process for producing a chromium yeast which comprises the steps of:

(1) dissolving an organochromium complex in distilled water to form an organochromium solution;
(2) filtering the organochromium solution through a filter;
(3) admixing the organochromium solution with live yeast culture to form a yeast-organochromium mixture;
(4) incubating the yeast-organochromium mixture with gentle shaking action;
(5) adding the yeast growth nutrients (growth medium) to the yeast-organochromium mixture to form a yeast-growing mixture;
(6) incubating the yeast-growing mixture for sufficient time to allow for yeast growth;
(7) isolating the yeast cells from the yeast-growing mixture;
(8) washing the isolated yeast cells to remove extracellular chromium; and
(9) pasteurizing and drying the washed yeast cells.

Chromium in the form of a chromium complex is used in the present invention which may be derived from a commercially available source [E.g., Chelavite®, Albion Laboratories, Inc.], or may be made by the process generally described above. More specifically, a chromium complex may be made by combining one mole of water soluble chromium with at least one mole of nicotinate salt and at least one mole of an amino acid salt, e.g., glycinate salts. In a preferred embodiment, chromium glycinate bisnicotinate may be used. Chromium complexes from either source are made into an organochromium solution by dissolving the organochromium complex in distilled water. For example, the organochromium complex using chromium Chelavite® may be prepared by adding 3.0 g of chromium Chelavite® to 300 mL of distilled water at ambient temperature. The resulting organochromium solution mixture is then warmed to 40–60° C. and incubated for 1 hour. The pH of the cooled homogeneous solution is adjusted to about 4.2.

The organochromium complex used should be at levels between about 200 ppm and 30,000 ppm of the chromium complex, and preferably about 500 ppm to about 25,000 ppm of the chromium complex, and most preferably between about 7,500 ppm and about 20,000 ppm of the chromium complex.

The organochromium solution is then filtered. In a preferred embodiment, a 0.4 micron cellulose acetate [Corning Scientific, Co.] is used. Other filters may be used, and one of skill in the art could readily determine which filters would be appropriate for filtering the organochromium solution.

The organochromium solution is then admixed with a live yeast culture to form a yeast-organochromium solution. The yeast culture employed in the present invention is preferably a food grade or edible yeast, and most preferably *S. cerevisiae*—commonly known as Brewer's yeast or Baker's yeast [Red Star] . Other yeast strains which can be used include Torula and *S. uvarum*.

The present invention also can employ a newly isolated and purified strain of Brewer's yeast, *Saccharomyces cerevisiae*, that yields dried yeast mass having an enriched content of the chromium ion of high biological activity. Specifically, *Saccharomyces cerevisiae* and *Saccharomyces boulardii sequela* are of the same genus, and *Saccharomyces boulardii sequela* is described as a synonym of *Saccharomyces cerevisiae*. [Barnett et al., Yeasts: *Characteristics and Identification*, Cambridge Univ. Press (1990)].

More particularly, the novel yeast strain of *Saccharomyces boulardii sequela* may be isolated from raw soil samples, and cultivated to yield quantities of yeast at a scale sufficient for developmental research and for production of commercial products. The novel strain of yeast of the invention, *Saccharomyces boulardii sequela* PY31, has been deposited in an International Repository in accord with the Budapest Treaty and has been assigned ATCC No. 74,366. The current address of the American Type Culture Collection (ATCC) is 10801 University Blvd., Manassas, Va. 20110. This novel yeast strain is described in co-pending application Serial No. 08/719,572 filed on September 25, 1996.

Specifically, the method for isolating this novel yeast strain, *Saccharomyces boulardii sequela* PY31, comprises:

(1) identifying a location for collection of a soil sample, which is proximal to a germanium mine (i.e., within 100 yards of a germanium mine);

(2) sampling the soil by removing about 200 g from a depth of 5 cm to 20 cm, and transporting the sample using a sterilized bag;

(3) growing the living material on three different mediums which support the growth of all yeast, and that selectively kills bacteria without killing the yeast;

(4) separating the yeast from other living matter and then repeating this process until yeast can be grown without bacterial contaminants;

(5) selecting and restreaking the yeast colonies, and repeating this process three times;

(6) selecting the yeast colonies most vital for growth in a medium enriched with germanium;

(7) growing each selected colony on malt extract agar or dextrose agar, and selecting which colonies appear most robust, and;

(8) cultivating the selected yeast by growing 1–2 slants of the yeast for about 2 days at about 30° C. and then transferring to the cultivated yeast about 100 mL of malt extract broth and then incubating at about 30° C. for 8–10 hours, then adding to the incubated mixture about 500 mL of malt extract broth and then growing the resulting mixture at about 30° C. for about 6 to about 14 hours.

The present invention teaches a use of the novel yeast strain *Saccharomyces boulardii sequela* PY31 for preparing chromium-enriched yeast forms according to the method described herein.

The yeast-organochromium solution is then incubated at a pH between about 3.8 to about 5.0, and preferably between about 4.0 to about 4.3. The incubation temperature may be from about 20° C. to about 35° C., and preferably between about 280C and about 32° C. The length of incubation of the yeast-organochromium solution may be from about 5 minutes to about 100 minutes, preferably from about 20 to about 100 minutes, and most preferably about 90 minutes. This incubation step may optionally include gentle shaking at 200 rpm.

After the yeast-organochromium solution (i.e., pregrowth) is incubated, growth media is added to induce growth, resulting in a yeast-growing mixture. Growth media that can be used in the present invention include 25° Brix molasses [TCT, Gold Coast] , 38° Brix molasses [TCT, Gold Coast], glucose media, and potato dextrose broth. Numerous other growth media that are known to support the growth of yeast from the Saccharomyces family may be used and could be readily selected by one of skill in the art. In addition, the growth media used in the invention may optionally include additional growth nutrients, including $KCl$, $MgSO_4$, and $NH_4H_2PO_4$. Other growth nutrients may be used and could be readily selected by one of skill in the art.

The yeast-growing mixture is then incubated for sufficient time to allow for yeast growth. This incubation step may optionally occur with gentle shaking at 200 rpm. The incubation lasts for at least 10 hours, preferably from between about 15 to about 60 hours, and most preferably between about 16 to about 20 hours. This incubation step occurs at a temperature of between about 25° C. and about 35° C., and preferably at about 30° C. Optionally, the growth medium may be autoclaved and cooled before addition of the yeast.

The yeast-growing mixture is then centrifuged to yield isolated yeast cells. The centrifugation occurs at between about 2500 and about 4500 rpm for between about 5 to about 60 minutes.

The isolated yeast cells are then washed several times to remove extracellular chromium. The initial wash material used in the present invention contains a buffer and a chelating agent. EDTA and $Na_2HPO_4$ are preferred components for the initial wash solution, and in a preferred embodiment, 0.1 M EDTA·0.01 M $Na_2HPO_4$. After the initial wash, the isolated yeast cells are washed four times with distilled water. Thus, in a preferred embodiment, the isolated yeast cells are washed once with 0.1M EDTA·0.01 M $Na_2HPO_4$ and four times with distilled water. The washed yeast cells are then pasteurized and dried in vacuo to yield a dried yeast product. The drying step may occur at about 100° C.

The dried chromium-yeast complexes of the present invention have a high intracellular content of organically bound trivalent chromium in a form, or forms, which are highly biologically active and non-toxic. The amount of chromium in the dried yeast product may be measured by atomic absorption. To accomplish this measurement, 0.1 g of the dried yeast sample is transferred to a 50 mL volumetric flask. To the flask, 5 mL of concentrated $HNO_3$ is added and left overnight at ambient temperature. The flask is then placed in a boiling water bath for four hours under a hood. After the flask is removed and its contents have cooled, distilled water is added in sufficient amount to fill the flask to its 50 mL volumetric line. The resultant solution is then filtered through #2 Whatman filter paper into a round bottom flask. Next, 1 to 10 mL of the sample is measured for its chromium content using an atomic absorption spectrometer [Perkin Elmer, 3100] set at a wavelength of 359.7 nm, a slit width of 0.7 nm, and a chromium lamp current at 25 mA.

The present invention also relates to the use of the dried chromium-yeast products as dietary supplements. To prepare the yeast compositions of the invention for use as a dietary supplement, the dried yeast product is combined as the active ingredient in intimate admixture with a suitable carrier according to conventional compounding techniques. This carrier may take a wide variety of forms depending upon the form of preparation desired for administration, e.g., oral, sublingual, nasal, or parenteral.

In preparing the compositions in oral dosage form, any of the usual pharmaceutical media may be employed. For oral liquid preparations (e.g., suspensions, elixirs, and solutions), media containing for example, water, oils, alcohols, flavoring agents, preservatives, coloring agents and the like may be used. Carriers such as starches, sugars, diluents, granulating agents, lubricants, binders, disintegrating agents, and the like may be used to prepare oral solids (e.g., powders, capsules, pills, and tablets). Controlled release forms may also be used. Because of their ease in administration, tablets, pills, and capsules represent advantageous oral dosage unit forms, in which cases solid pharmaceutical carriers are obviously employed. If desired, tablets may be sugar coated or enteric coated by standard techniques.

For parenteral products the carrier will usually comprise sterile water, although other ingredients may be included, e.g., to aid solubility or for preservation purposes. Injectable suspensions may also be prepared, in which case appropriate liquid carriers, suspending agents, adjuvants, and the like may be employed.

A composition of the present invention is generally effective when parenterally administered in amounts ranging from about 1 mg of dried yeast per dose (1 dose per body weight of about 75 kg) to about 1000 mg/dose of composition. When orally administered, the compositions of the present invention are generally effective in approximately the same amounts as the parenteral products. Activity at this level makes the compositions particularly well suited for formulations in tablet size for oral administration. The above dosage ranges are likely to be administered at varying periods for humans, for example, from daily administration to administration at least 5 times per week. However, ultimately, the dosage regimen will depend upon the particular needs of the user. A preferred dosage regimen for humans is 1–2 doses per day.

The following examples are illustrative only and do not limit the invention in any fashion.

EXAMPLE 1

A stock solution of chromium glycinate bisnicotinate was prepared as follows. To 300 mL of distilled water at ambient temperature was added 3.0 g of chromium glycinate bisnicotinate and the resulting mixture was warmed to 40–60° C. and incubated at that temperature for 1 hour. The solution was then cooled to 25° C., and the pH of the cooled homogeneous solution was adjusted to 5.2. The resultant solution was then filtered through a 0.45 micron cellulose acetate membrane [Corning Scientific Co.].

The growth medium was prepared as follows. About 670 g of 790 Brix molasses [TCT, Gold Coast] was diluted to 1 L with distilled water, followed by addition of 2.72 g of KCl, 2.72 g of $MgSO_4$, and 29.28 g of $NH_4H_2PO_4$. The resultant solution was stirred to homogeneity. To this solution was added a sufficient quantity of distilled water to reach a final volume of 2 L. The mixture was tested for sugar content by using a hydrometer—optimal sugar content being 25° Brix content. The final pH was then adjusted to 3.5 to 5.0.

This growth medium was then autoclaved at 121° C. for 15 minutes to prepare for the addition of cultivated yeast. The yeast were cultivated as follows. To 250 mL of the stock chromium solution was added 2.5 g of Brewer's yeast [Red Star] and the resulting suspension was shaken for 40 minutes. Next, 60 mL of the 25° Brix molasses solution described above was added and the resulting mixture was shaken at 200 rpm for about 17.5 hours at 30° C. The resultant mixture was centrifuged at 3,900 rpm for 5 to 10 minutes, the supernatant was removed, and then the yeast cells were washed once with a solution of 100 mL of 0.1 M EDTA (pH 6.5) and 0.01 M $Na_2HPO_4$ buffer solution, and then four times with 100 mL of distilled water. The resulting yeast cream was dried in vacuo at about 100° C. and then the chromium content of the yeast was measured using atomic absorption techniques described above.

EXAMPLE 2

This example describes the results of experiments directed towards understanding the relationship between absorption time and yeast concentration.

A stock solution and growth medium were prepared as described in Example 1. The yeast were cultivated in three separate experimental groups (in three separate flasks) as follows. To each flask, 250 mL of the stock chromium solution was added followed by the addition of 0.5 g or 1.0 g, or 1.5 g of Brewer's yeast [Red Star] in each respective flask. The resulting suspensions were shaken for 0, 40, or 90 minutes respectively. Then, 60 mL of 25° Brix molasses [TCT, Gold Coast] solution was added to each of the three flasks and the resulting mixtures were shaken at 200 ppm for 24 hours at 30° C. These mixtures were centrifuged at 3,900 rpm for 10 minutes, the supernatants removed, then the yeast cells in each flask were washed successively once with 100 mL of 0.1 M EDTA·0.01 M $Na_2HPO_4$ buffer solution (pH 7.8), and then four times with 100 mL of distilled water.

The resulting yeast cream from each flask was dried in vacuo and then the chromium content of the yeast was measured using atomic absorption techniques. The results are shown below in Table 1.

TABLE 1

Comparison of Absorption Time and Amount of Yeast

| initial yeast (g) | absorption time (min.) | [Cr] (ppm) |
|---|---|---|
| 0.5 | 0 | 1654 |
| 1.0 | 0 | 1557 |
| 1.5 | 0 | 1204 |
| 0.5 | 40 | 3167 |
| 1.0 | 40 | 4123 |
| 1.5 | 40 | 4090 |
| 0.5 | 90 | 4066 |
| 1.0 | 90 | 4924 |
| 1.5 | 90 | 4790 |

EXAMPLE 3

This example describes the results of experiments directed towards understanding the relationship between the concentration of chromium ion in the growth media and final chromium concentration in the dried yeast product.

The stock solution and growth medium were prepared as described in Example 1. The yeast were cultivated as follows. In five separate flasks containing 250 mL, 187.5 mL, 125 mL, 62.5 mL, or 25 mL of the stock chromium solution, 0 mL, 62.5 mL, 125 mL, 187.5 mL, or 225 mL of distilled water was added respectively. Then, 2.5 g of Brewer's yeast [Red Star] was added to each flask and the resulting suspension was shaken for 40 minutes at 200 rpm. Then 60 mL of 25° Brix molasses [TCT, Gold Coast] solution was added to each flask and the resulting mixtures were shaken at 200 rpm for 24 hours at 30° C. The mixtures were then centrifuged at 3,900 rpm for 10 minutes, the supernatant removed, then the yeast cells were successively washed once with 100 mL of 0.1 M EDTA·0.01 M $Na_2HPO_4$ buffer solution (pH 7.8), and four times with 100 mL of distilled water.

The resulting yeast cream was dried in vacuo and then the chromium content of the yeast was measured using atomic absorption techniques. The results are shown below in Table 2.

TABLE 2

Chromium Concentration in Growth Media at 17.5 hr. Incubation Time

| Stock Solution (mL) | [Cr] growth (ppm) | [Cr] final yeast (ppm) |
|---|---|---|
| 250 | 8,064 | 3820 |
| 187.5 | 6,048 | 3487 |
| 125 | 4,032 | 2048 |
| 62.5 | 2,016 | 1085 |
| 25 | 806 | 487 |

EXAMPLE 4

This example describes the results of an experiment that uses the new yeast strain *Saccharomyces boulardii sequela* PY31 described above.

The stock solution and growth media were prepared as described in Example 1. To a 2 L beaker was added 160 mL of chromium Chelavite® solution [Albion Laboratories, Inc.] and 490 mL of distilled water. This organochromium solution was then filtered through a cellulose acetate filter. Next, 150 mL of the yeast strain *Saccharomyces boulardii*

*sequela* PY31 (ATCC No. 74,366) at a concentration of about 1–2×10⁶ per mL was added. The resulting mixture was shaken at 200 rpm at ambient temperature for 90 minutes. Then, 158 mL of 38° Brix molasses solution was added and the resultant mixture was shaken at 200 rpm for 16 hours at 30° C. The mixture was then centrifuged at 3900 rpm for 10 minutes, the supernatant removed, and the yeast cells successively washed once with 100 mL of 0.1 M EDTA·0.1 M Na$_2$HPO$_4$ buffer solution (pH 7.8), and four times with 100 mL distilled water. The resulting yeast cream was dried in vacuo and the chromium content of the yeast was measured using atomic absorption techniques to yield a yeast material having a chromium content of 3537 ppm.

Numerous modifications and variations of the present invention are included in the above-identified specification and are expected to be obvious to one of skill in the art. It is also intended that the present invention cover modifications and variations of the dried yeast chromium compositions and method for using them to accomplish their claimed uses within the scope of the appended claims and their equivalents.

We claim:

1. A method of producing an edible chromium yeast product comprising:
    a) admixing a live yeast culture with an organochromium solution comprising about 500 ppm to about 25,000 ppm chromium glycinate dinicotinate to form a yeast-organochromium mixture;
    b) incubating the yeast-organochromium mixture for about 5 to about 100 minutes;
    c) adding growth media to the yeast-organochromium mixture to form a yeast-growing mixture;
    d) grow the yeast in the yeast-growing mixture for at least 10 hours;
    e) isolating the yeast from the yeast-growing mixture;
    f) washing the yeast to remove extracellular chromium glycinate dinicotinate; and
    e) pasteurizing and drying the washed yeast cells to yield the chromium yeast product.

2. The method of claim 1 wherein the live yeast culture is selected from the group consisting of: *Saccharomyces cerevisiae, Saccharomyces uvarum*, Torula spp., and *Saccharomyces boulardii sequela* PY3 1 (ATCC No. 74,366).

3. The method of claim 1 wherein the organochromium solution comprises about 7,500 ppm to about 20,000 ppm chromium glycinate dinicotinate.

4. The method of claim 1 wherein the yeast-organochromium mixture is incubated for about 20 to about 100 minutes.

5. The method of claim 1 wherein the yeast-organochromium mixture is incubated for about 40 minutes.

6. The method of claim 1 wherein the yeast-organochromium mixture is incubated for about 90 minutes.

7. The method of claim 1 wherein the yeast-growing mixture is grown for about 15 to about 60 hours.

8. The method of claim 1 wherein the yeast-growing mixture is grown for about 16 to about 20 hours.

9. The method of claim 1 wherein the pH of the yeast-organochromium mixture is adjusted to be within the range of from about pH 3. to about pH 5.0.

10. The method of claim 1 wherein the pH of the yeast-organochromium mixture is adjusted to be within the range of from about pH 4.0 to about pH 4.3.

11. The method of claim 1 wherein the yeast-organochromium mixture is incubated at a temperature in the range of from about 20° C. to about 35° C.

12. The method of claim 1 wherein the yeast-organochromium mixture is incubated at a temperature in the range of from about 20° C. to about 35° C.

13. The method of claim 1 wherein the chromium yeast product has an intracellular organically complexed chromium content of from about 4066 ppm to about 4924 ppm.

14. The method of claim 1 wherein the live yeast culture is *Saccharomyces boulardii sequela* PY31 (ATCC N6. 74,366).

15. A chromium yeast product produced according to the method of claim 1 wherein the chromium yeast product has an intracellular organically complexed chromium content of from 1000 ppm to 6000 ppm.

16. The chromium yeast product of claim 15 wherein the chromium yeast product has an intracellular organically complexed chromium content of frown about 4066 ppm to about 4924 ppm.

17. A dietary supplement comprising a chromium yeast product produced by the method of claim 1 and a pharmaceutical carrier for formulation into an oral dosage form.

18. The dietary supplement of claim 17 wherein the oral dosage from is selected from the group consisting of tablets, pills, and capsules.

19. The dietary supplement of claim 17 wherein the supplement comprises 1 mg to 1000 mg of the chromium yeast product.

* * * * *